United States Patent [19]
Sato et al.

[11] Patent Number: 6,090,791
[45] Date of Patent: Jul. 18, 2000

[54] METHOD FOR INDUCING MUCOSAL IMMUNITY

[75] Inventors: Yukio Sato, 59-2-202, Yanagikoji, Watari, Fukushima-shi; Atsushi Irisawa, Fukushima; Ayako Saito, Fukushima; Reiji Kasukawa, Fukushima, all of Japan

[73] Assignees: Taisho Pharmaceutical Co., Ltd.; Yukio Sato, both of Japan

[21] Appl. No.: 09/123,312

[22] Filed: Jul. 28, 1998

[30] Foreign Application Priority Data

Jan. 22, 1998 [JP] Japan .................................. 10-010093

[51] Int. Cl.[7] .......................... A61K 31/00; A61K 39/00; C07H 21/04
[52] U.S. Cl. ......................... 514/44; 424/184.1; 536/23.1
[58] Field of Search ........................... 514/44; 424/184.1; 536/29.1

[56] References Cited

U.S. PATENT DOCUMENTS 5,663,153  9/1997  Hutcherson et al. ...................... 514/44

OTHER PUBLICATIONS

Etchart et al. Class I–restricted CTL induction by mucosal immunization with naked DNA encoding measles virus haemagglutinin. J. Gen. Virol. 78: 1677–1580, 1997.

Ban et al. Mucosal immunization with DNA encoding influenza hemagglutinin. Vaccine. 15 (8): 811–813, 1997.

Fynan et al. DNA vaccines: Protective immunizations by parenteral, mucosal, and gene–gun inoculations. PNAS. 90: 11478–11482, Dec. 1993.

David Pisetsky, "The Immunologic Properties of DNA," 421–423, 1996.

Sato Y., et al., "Immunostimulatory DNA Sequences Necessary for Effective Intradermal Gene Immunization," 1996, p. 352–354.

Roman et al, "Immunostimulatory DNA sequences function as T helper–1–promoting Adjuvants," 1997, p. 849–854.

*Primary Examiner*—Nancy Degen
*Attorney, Agent, or Firm*—Lorusso & Loud

[57] ABSTRACT

By injecting plasmid DNAs or oligonucleotides with DNA sequence containing a 2 base sequence of unmethylated cytosine and guanine adjacent thereto into mamalian mucosal cells, mucosal immunity and CD4 positive T cells capable of producing interleukin 10 and IFN-γ can be induced.

4 Claims, 1 Drawing Sheet

METHOD FOR INDUCING MUCOSAL IMMUNITY

BACKGROUND OF THE INVENTION

1. Field of the Invention

The present invention relates to a method for inducing mucosal immunity which comprises a nucleic acid containing immunostimulatory DNA sequence (ISS) to human mucosal membrane.

2. Related Art Statement

Throughout the history of genetic recombinant technology, plasmid DNA (pDNA) of bacterial origin has been recognized to be essential for cloning of useful genes and for mass production of useful proteins.

As a new application of these pDNAs, DNA vaccination has been proposed. This technology is based on the finding that by direct injection of pDNA with antigenic protein-encoding gene into the quadriceps femoris muscle of mice, a protein encoded by pDNA was expressed in the muscle cells and induced an immune response to the expressed protein.

Following the above finding, it has been reported that oligonucleotides (ODNs) containing a two base sequence of unmethylated cytosine and guanine next thereto (CpG motifs), which are present in bacterial DNA, or CpG motif-containing pDNAs themselves stimulate lymphocytes/monocytes to induce several cytokines such as interleukin 6 and interleukin 12 (Pisetsky S. D. et al., J. Immunol, 156, 421, 1996). These DNA sequences, termed immunostimulatory DNA sequences (ISSs), have been reported to have the function of inducing the production of T helper-1 (Th1) type cytokines by monocytes. It is known that the Th1 type systemic immunity can be induced by injection of pDNA with ISS through production of interferon γ (IFN-γ) or interleukin 12 (IL-12) stimulated by ISS in pDNA (Sato Y., et al., Science, 273, 352, 1996).

SUMMARY OF THE INVENTION

The present invention provides a method for inducing mucosal immunity, utilizing a newly discovered function of the nucleic acid with ISS.

In the process of investigating ISSs, the present inventors have found that by injecting a nucleic acid containing the ISS into mucosal cells, mucosal immunity is induced and, unexpectedly, this immunization induces CD4+ T cells producing both interleukin 10 (IL-10) and IFN-γ, unlike the systemic immunization which induces Th1 cells producing IFN-γ, but not IL-10. The present invention has thus been accomplished.

That is, the present invention relates to a method for inducing mucosal immunity which comprises administering a nucleic acid with ISS to human.

DESCRIPTION OF THE PREFERRED EMBODIMENTS

ISSs which can be used in the present invention are oligonucleotides comprising a 2 base sequence (CpG motifs) of unmethylated cytosine and guanine adjacent thereto, as described above. As specific nucleic acids containing the above sequence, pACB-Z, pACS-Z, pKISS-1-CB-Z, pUCl9 and others are reported in Sato Y., et al., Science, 273, 352, 1996; and Roman et al., Nature Medicine, 3, 849, 1997. Though these specific examples of the nucleic acids are pDNAs or circular DNAs, linear nucleic acids can also be used for the present invention, so long as the nucleic acids contain the ISSs.

The nucleic acids with ISSs can be prepared into appropriate pharmaceutical preparations, e.g., in the form of a solution. Direct injection of such preparations into mucosal cells such as the gastric wall, the oral cavity, the nasal cavity, etc. can elicit mucosal immunity. It may be advantageous to make preparations of inclusion type using liposomes that can improve transfer of the nucleic acid into the mucosal cells. For example, the nucleic acid with ISSs is incorporated into liposomes to prepare liposome preparations, by technique known for such pharmaceutical preparations. These liposome preparations can be administered orally or pernasally.

The nucleic acid with ISSs used in the present invention can be commercially available pDNA generally supplied for experimental use. Such pDNA may be used directly in its commercially available form, or may also be used after amplification in an appropriate host such as E. coli, etc., using conventional genetic engineering technique.

For injection of the thus prepared nucleic acid with ISSs into mucosal cells, it is preferred to use a solution of the nucleic acid in a suitable buffer solution. The suitable buffer solution can be chosen from buffer solutions of Tris type, phosphate type, citrate type and acetate type.

Thus, the mucosal immunity inducer of the present invention which elicits mucosal immunity by the direct action on mucosal cells is effectively applicable to the treatment of allergic diseases represented by asthma and rhinitis.

The present invention will be described in more detail, with reference to the following examples.

EXAMPLE 1

1) Administration of ISS-containing pDNAs (ISS-pDNA) to mice

Figure 1:
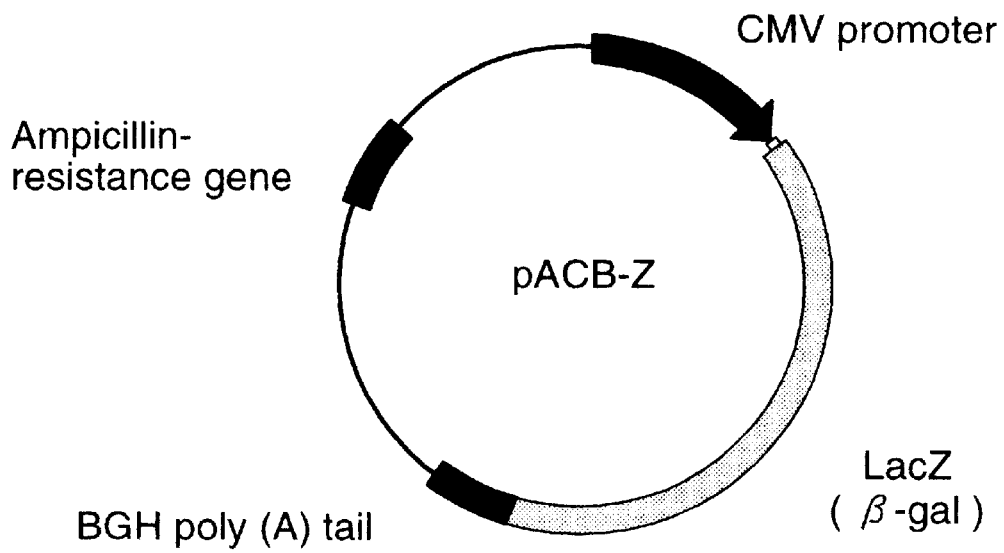
FIG. 1 shows the structure of pACB-Z which is a nucleic acid containing ISSs (sequence: 5'-AACGTT-3'), pACB-Z is a plasmid DNA (pDNA) containing Lac Z encoding β-galactosidase, a cytomegalovirus (CMV)-derived promoter and, ampicillin-resistance gene.

PACB-Z with ISSs sequence shown in FIG. 1 was dissolved in physiological saline in a concentration of 1 μg/μl. After laparotomy, four (4) Balb/c mice were immunized with 20 μl of the pACB-Z solution through intra-gastric injection (i.g.) from the serosa into the stomach wall. For comparison, four (4) Balb/c mice were similarly immunized with 20 μl of the pACB-Z solution by intradermal injection (i.d.). After feeding for 3 weeks under the same conditions, the feces were collected from the animals.

2) Confirmation of induced mucosal immunity

2)-1) Measurement of IgA antibody

Figure 2:
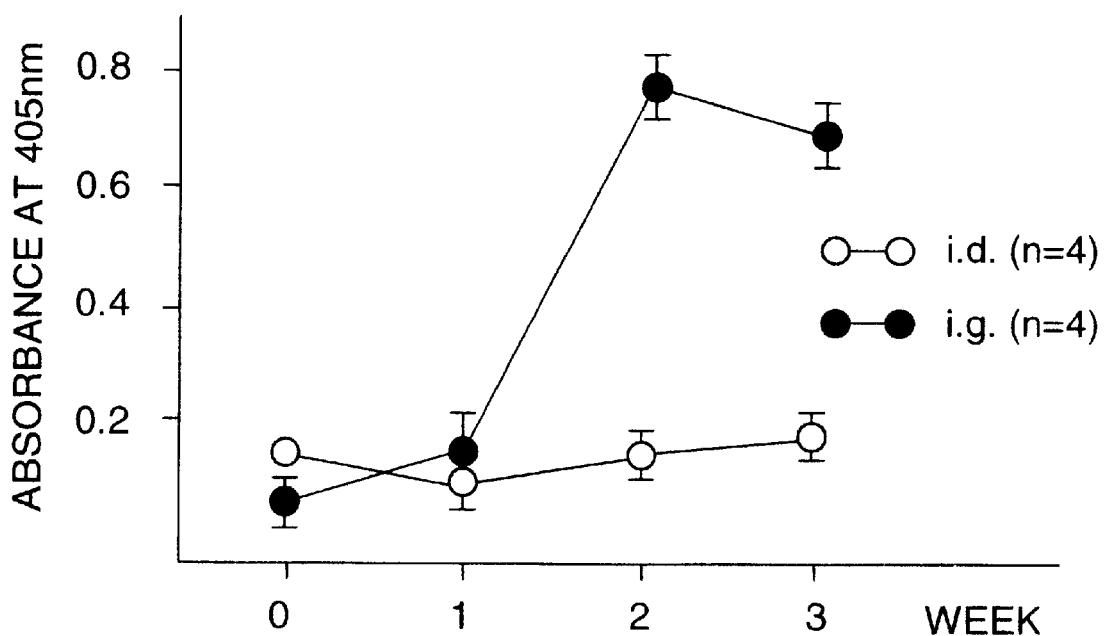
FIG. 2 shows a change of β-gal specific IgA antibody titer determined in the feces of pACB-Z immunized mice, wherein the change is observed with lapse of weeks. In the figure, symbols ○ and ● denote a change in the antibody titer of mice when the nucleic acid with ISS sequence was given through intradermal injection and intra-gastric injection, respectively.

After boosting and feeding the mice in 1) above, the feces were collected from the mice every week. β-Galactosidase (β-gal) specific IgA antibody in the feces was determined by ELISA, in which β-gal protein had been immobilized and alkaline phosphates labeled anti-mouse IgA antibody (made by Southern Biotechnology Inc.) was used as a developing antibody. The results are shown in FIG. 2.

The mice that received pACB-Z by intra-gastric injection induced the production of β-gal specific IgA antibody in the feces, whereas in the mice intradermally injected with pACB-Z, there was no significant change in the amount of β-gal specific IgA antibody expressed in the feces. The results reveal that by injection of the nucleic acid with ISSs into mucosal cells, mucosal immunity was specifically induced.

2)-2) Measurement of cytokine expressed

After feeding the mice immunized in 1) above for 8 weeks, CD4-positive T cells were purified from the spleen cells by the deletion technique using anti-CD8 antibody and complement. Irradiated T cell-free spleen cells were added as antigen presenting cells to the purified CD4-positive T cells and coincubated with β-gal protein. After incubation for 3 days, IFN-γ, interleukin 4 (IL-4) and IL-10 were measured in the supernatant. These cytokines were assayed using the ELISA Kit made by Endogen Inc. The results are shown in Table 1 below.

TABLE 1

| Administration Route for pACB-Z | Measurement of Cytokine | | | Feces Secretory IgA Antibody |
|---|---|---|---|---|
| | CD4 Positive T Cell | | | |
| | IFN-γ | IL-4 | IL-10 | |
| i.d. injection | + | − | − | − |
| i.g. injection | + | − | + | + |

The results shown in Table 1 reveal that the mice intradermally injected with pACB-Z merely produced IFN-γ alone. On the other hand, the PACB-Z injected mice (i.g.), IL-10 was further produced, in addition to IFN-γ; that is, injection of the nucleic acid with ISSs into mucosal cells induced, CD4+ T cells producing both TH1 type cytakine, IFN-γ, and Th2 type cytokine, IL-10 and mucosal immunity.

What we claim is:

1. A method for inducing interleukin 10 (IL-10)-producing Th2 type mucosal immunity, said method comprising administering a nucleic acid with immunostimulatory sequences (ISSS) to a human whereby the mucosal immunity is induced.

2. The method according to claim 1, wherein said nucleic acid is injected into human mucosal cells.

3. The method according to claim 1, wherein said nucleic acid is an oligonucleotide containing a CpG motif.

4. The method according to claim 1, wherein said nucleic acid has a nucleotide sequence of AACGTT.

* * * * *